United States Patent [19]
Coulston et al.

[11] 3,959,492
[45] May 25, 1976

[54] METHOD FOR REDUCING SERUM BLOOD CHOLESTEROL

[75] Inventors: Frederick Coulston, Schenectady; Ira Rosenblum, Rensselaer, both of N.Y.

[73] Assignee: Istituto Chemioterapico Italiano, Milan, Italy

[22] Filed: Jan. 10, 1975

[21] Appl. No.: 539,955

Related U.S. Application Data

[62] Division of Ser. No. 313,344, Dec. 8, 1972, Pat. No. 3,873,273.

[52] U.S. Cl. .............................................. 424/324
[51] Int. Cl.² ...................................... A61K 31/165
[58] Field of Search ........................... 424/319, 324

[56] References Cited
UNITED STATES PATENTS
3,769,334   10/1973   Garzia................................ 424/309

Primary Examiner—Stanley J. Friedman
Attorney, Agent, or Firm—Morton, Bernard, Brown, Roberts & Sutherland

[57] ABSTRACT

A method of lowering blood cholesterol using 3,4,5-trimethoxybenzoyl-5-amino caproate sodium and related compounds is disclosed.

1 Claim, No Drawings

METHOD FOR REDUCING SERUM BLOOD CHOLESTEROL

This is a division of application Ser. No. 313,344, filed Dec. 8, 1972, now U.S. Pat. No. 3,873,273.

The present invention is directed to a blood cholesterol lowering agent characterized in that it is a compound having the formula:

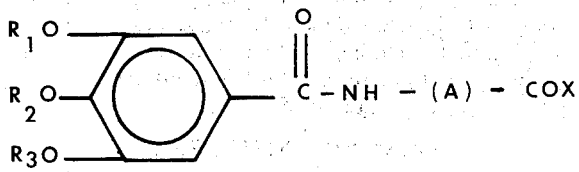

wherein $R_1$, $R_2$, and $R_3$ are hydrogen, methyl, ethyl, or propyl, and A is a saturated hydrocarbon radical of 3 to 8 carbon atoms or a saturated hydrocarbon radical substituted with one carboxylic acid group and containing 2 to 8 carbon atoms, and X is —OH, —$NH_2$ or —$OR_4$ where $R_4$ is lower alkyl, or a pharmaceutically-acceptable salt thereof.

Atherosclerosis is characterized by fatty degeneration occurring in the arterial walls, although the underlying mechanism has not been definitively established. It has been observed, however, that hypercholestermia is a common finding in mammals and other animals with atherosclerosis. Hypercholesteremia refers essentially to an excess of cholesterol in the blood serum. While the causes of hypercholesteremia and the nature of its role in atherosclerosis and related conditions is not clearly understood, considerable effort has been directed toward reducing blood and tissue cholesterol levels as an attack on the clinical conditions in which high levels are implicated. It has long been recognized that certain substances such as sitosterol, corn oil, and nicotinic acid are capable of reducing in small degree the blood tissue cholesterol contents, either by interfering with the absorption or exogenous cholesterol introduced with food, or by facilitating in some manner the excretion of cholesterol from the body. Major emphasis, however, has been placed on the search for additional compounds which offer a more positive means for control of cholesterol levels.

These compounds and their use for treating myocardial infarction patients are known. The use of these compounds as blood cholesterol lowering agents has not previously been disclosed prior to the present invention. This new use is the present invention. Agents which are normally used for treating myocardial infarction patients are not used, nor are they considered as being capable of use as blood cholesterol lowering agents. Therefore, the present invention is totally unexpected by the skilled artisan. Preferably, the therapeutically-acceptable salts of the compounds of the present invention are water-soluble neutral salts, e.g. sodium of potassium salts. Other suitable salts are, for example, the ammonium, magnesium or calcium salts of the free acid.

The acids of this invention include, for example, (3,4,5-trialkoxybenzoyl)amino alkanoic acids such as (3,5-diethoxy-4-methoxybenzoyl)-ε-amino caproic acid, (3,4,5-triethoxybenzoyl)-ε-amino caproic acid, (4-ethoxy-3,5-dimethoxybenzoyl)-ε-amino caproic acid; (3,4,5-tripropoxybenzoyl)-ε-amino caproic acid; N-(3,4,5-trimethoxybenzoyl)-L-isoleucine; N-(3,4,5-trimethoxybenzoyl)-DL-norvaline: N-(3,4,5-trimethoxybenzoyl)-L-leucine, (3,4,5-triethoxybenzoyl)-δ-amino isovaleric acid, N-(3,4,5-tripropoxybenzoyl)-L-leucine, N-(3,4-dipropoxy-5-ethoxybenzoyl)-L-isoleucine, and others. (3,4,5-trialkoxy benzoyl)amino dialkanoic acids include N-(3,4,5-trimethoxybenzoyl)-L-glutamic acid, N-(3,4,5-triethoxybenzoyl)-L-aspartic acid, N-(3,4,5-tripropoxybenzoyl)-γ-amino adipic acid; N-(3,5-dimethoxy-4-ethoxybenzoyl)-α-amino pimelic acid, N-(3,4,5-trimethoxybenzoyl)-α-amino suberic acid, N-(3,4,5-trimethoxy benzoyl)-L-aspartic acid, N-(3,4,5-trimethoxybenzoyl)-α-amino adipic acid, N-(3,4,5-trimethoxybenzoyl)-L-glutamine, N-(3,4,5-trimethoxybenzoyl)-L-aspargine, and others. (3,4,5-dialkoxymonohydroxybenzoyl)-amino alkanoic acids include syringoyl-ε-amino caproic acid, (3,4-diethoxy-5-hydroxybenzoyl)-δ-amino valeric acid, (3,5-diethoxy-4-hydroxybenzoyl)-γ-amino butyric acid; (3,4-dipropoxy-5-hydroxybenzoyl)-ζ-amino heptanoic acid, and others.

The (3,4,5-trimethoxy-benzamido)-alkanoic acid are a preferred group and include γ-(3,4,5-trimethoxybenzamido)-butyric acid, δ-(3,4,5-trimethoxybenzamido)-valeric acid, ε-(3,4,5-trimethoxybenzamido)-caproic acid, ζ-(3,4,5-trimethoxybenzamido-heptanoic acid, η-(3,4,5-trimethoxybenzamido)-octanoic acid, θ-(3,4,5-trimethoxybenzamido)-nonaoic acid and others.

The compounds of the present invention are prepared by reacting the appropriate benzoyl chloride, e.g. 3,4,5-trialkoxy benzoyl chloride with the appropriate aminoalkanoic acid, i.e. $NH_2$—A—COOH such as $NH_2$—$(CH_2)_x$—COOH, where $x$ is 3 to 8, at a temperature of about −5° to +5°C. According to the process of this invention, the free amino acid is slurried in about an equal weight of water and is neutralized with sodium hydroxide solution (about 30% by weight). Excess sodium hydroxide is added to promote the reaction. The mixture is chilled to within −5°C. to +5°C., and the trisubstituted benzoyl chloride is gradually added with agitation, maintaining the temperature at below 5°C. The mole ratio of amino acid to the acid chloride is generally about 1–1.5:1. The resulting solution is stirred for from two to four days and when the reaction is complete can be treated with char to decolorize it. It is then neutralized with dilute HCl or $H_2SO_4$ to about a pH of 3 or a Congo red indicator endpoint. The resulting precipitate is separated, e.g. by filtration, centrifugation or decantation and dried. The preparation of the acids is described in detail in U.S. Pat. Nos. 3,769,335; 3,692,827; 3,726,913; 3,697,563; and 3,769,334.

The pharmaceutically-acceptable salts of the free acid compound of the present invention can be obtained in any convenient manner. For example, the free acid can be converted into the salts by reaction with an appropriate base in the presence of an inert solvent. Appropriate bases are, for example, sodium hydroxide, potassium hydroxide, ammonium hydroxide, magnesium hydroxide, and calcium hydroxide.

The dosage of the principal active ingredients, e.g., (3,4,5-trialkoxybenzoyl)amino alkanoic acid of this invention in mammals and animals must be determined individually by according to the subject's age, weight, response to the medication, severity of the condition being treated, and the route of administration. The dosages generally range from about at least 1 mg/kg/day (milligrams per kilogram body weight per day), preferably 1 to 5000 mg/kg/day, more preferably 2 to 2000 mg/kg/day. The treatment can consist of a single daily dose, or the above dosages can be given fractionally at periodic intervals, for example, two to four doses of about 5 to 500 mg/kg can be administered per day. In adapting the present compositions to veterinary practice, the dosage should be adjusted on an appropriate weight ratio basis.

In adapting the active ingredients for use in mammals, the compounds are suitably presented for administration in unit dosage forms as tablets, pills, capsules, powders, wafers, cachets, granules, sterile parenteral solutions or suspensions in aqueous or oil vehicles, oral aqueous or oil dispersions, including syrups and elixirs, and the like. When the active materials are used as a parenteral solution for injection, e.g. subcutaneous intraperitoneal, percutaneous, intravenous, intraarterial, intracutaneous, intramuscular, or interarticular injection, they are preferably in the form of the corresponding water-soluble neutral salt, preferably the sodium salt.

For preparing solid compositions such as tablets, the active ingredient is mixed with a conventional tableting component such as cornstarches, lactose, dicalcium, phosphate, talc, stearic acid, calcium stearate, gums, and functionally similar materials constituting pharmaceutical diluents, lubricants, granulating agents, or carriers. The tablets or pills can be laminated or otherwise compounded to provide a dosage form affording the advantage of prolonged or delayed action or of predetermined successive action of the enclosed medication. For example, the tablet or pill can comprise an inner dosage and outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate phthalate (as described in U.S. Pat. No. 2,196,768) and the like.

The liquid forms in which the novel composition of this invention can be incorporated include aqueous dispersions, suitably flavored syrups, emulsions or suspensions with edible oils such as corn oil, cottonseed oil, safflower oil, soybean oil, and the like, as well as elixirs and similar pharmaceutical vehicles. Suitable dispersing or suspending agents for aqueous suspensions include the synthetic and natural gums such as tragacanth, acacia, alginate, dextran, methylcellulose, polyvinylpyrrolidone, gelatin, and the like.

For injectable solutions or suspensions, conventional preservatives, buffers, isotonic agents and suspending agents are advantageously employed. Suitable preservatives include chlorobutanol, myristyl gamma picolinium chloride, benzyl alcohol, the methyl- and propylparabens, and sodium ethyl mercurithiosalicylate. Potassium chloride is preferred as an isotonic agent. Among the suspending agents which are suitable for present purposes are polyethylene glycol 4000 or 6000, polyvinylpyrrolidone, dextran, methylcellulose, and surfactants such as polysorbate 80.

To demonstrate the effect of the components of this invention upon serum blood cholesterol, 34 rhesus monkeys (*Macaca mulatta*), 18 males and 16 females, were studied, including oral and intravenous administration of the drug 3,4,5-Trimethoxybenzoyl-$\epsilon$-Aminocaproate Sodium (TBAC).

ORAL ADMINISTRATION 16 monkeys were divided into groups so that 3 males and 3 females would receive 3000 mg/kg/day and 3 males and 3 females would receive 750 mg/kg/day of the drug in aqueous 1 percent gum tragacanth, while 3 males and 1 female monkey would serve as controls and receive only the vehicles.

INTRAVENOUS ADMINISTRATION 18 rhesus monkeys, 9 of each sex, were divided into groups so that 6 received 800 mg/kg/day and 6 received 125 mg/kg/day of the drug, while 6 monkeys were controls. The drug was injected intravenously as a sterile solution into a superficial vein daily for the first 5 days of the first week and then 3 times weekly over the remaining weeks. Control monkeys received injections of sterile saline solution.

General observations were made daily and individual weights were recorded weekly. Baseline values were made of erythrocyte, leukocyte, and differential counts, hemoglobin and hematocrit, and of serum chemistry including calcium, phosphate, glucose, blood urea nitrogen, uric acid, cholesterol, total protein, albumin, bilirubin, LDH, and SGOT using an Autoanalyzer SMA 12/60.

Additional values were also obtained at 30, 60, and 90 days in the oral study, and at 30 days in the intravenous study. Statistical comparisons were made by paired data, single-tail t-test (Goldstein, 1964).

Administration of TBAC to rhesus monkeys by either the oral and intravenous route produced a significant fall in serum total cholesterol as shown in the following table. This effect of the drug appears to be dose-dependent. The earliest evidence for this change was after 30 days of oral or intravenous administration, but the effect is also persistent, as long as the drug is administered, for it was still evident after 90 days.

TABLE

SERUM CHOLESTEROL (MG/100CC + SE) IN RHESUS MONKEYS GIVEN
3,4,5-TRIMETHOXYBENZOYL-$\epsilon$-AMINOCAPROATE SODIUM

| | Oral Administration | | | Intravenous Administration | | |
|---|---|---|---|---|---|---|
| Time | Control | 3,000 mg/kg/day | 750 mg/kg/day | Control | 800 mg/kg/day | 125 mg/kg/day |
| Baseline | 157±18 | 231±18 | 181±10 | 168±13 | 170±8 | 190±17 |
| 30 days | 173±10 | 140±35$^a$ | 190±10 | 163±13 | 133±2$^a$ | 164±15 |
| 60 days | 181±20 | 167±18$^a$ | 188±15 | | | |
| 90 days | 165±12 | 131±5$^a$ | 171±13 | | | |

$^a$vs. baseline value, p<.05.

The effects of 3,4,5-trimethoxybenzoyl-$\epsilon$-aminocaproate sodium (TBAC) on healthy human volunteers has been determined in a safety evaluation of TBAC, a new drug for use in myocardial infarction, carried out on 26 racially mixed, healthy volunteers between the ages of 24 to 49 years. The drug was given at various dose levels orally (2, 4, and 8 grams/day) and intravenously (2 gram/day). The 26 volunteers were divided into four groups, three of which received the drug or placebo orally at different does levels. The fourth group received the drug or placebo intravenously and subsequently received the drug or placebo orally. Drug and placebo were randomly assigned to the members of each group. The studies were done double blind in the first three groups and single blind in the fourth group.

Group I consisted of six subjects. Four subjects received the drug, provided in 0.5 g tablets, at a dose of 2 g/day divided into two equal doses. The remaining two subjects received an equivalent number of placebo tablets.

After Group I had received the drug or placebo for one week, during which time no significant complaints were reported, Group II, similarly constituted, was started at a dose of 4 g/day divided into two equal doses. This dosage schedule was continued for two weeks.

After Group II had received their drug or placebo for one week without any significant complaints, Group III, similarly constituted, was started at a dose of 8 g/day divided into two equal doses. The dosage schedule was continued for one week.

Group IV consisted of eight subjects. Six of these received 2 g of the drug dissolved in one liter of Plasmalyte R-148 (Travenol) by intravenous drip over a period of eight hours each day for five consecutive days, followed by oral administration of the drug at a dose of 4 g/day for two weeks. Two subjects serving as controls received the Plasma-lyte solution without the drug concurrently with the experimental subjects, followed by oral administration of the placebo.

No significant complaints were reported by the subjects, and no significant pharmacologic changes were observed as measured by the electrocardiogram, blood pressure, and pulse rate. Baseline clinical chemistry and hematologic values remained within normal limits with the important exception of serum total cholesterol which showed a significant reduction, particularly at two dose levels: 8 grams/day orally for one week and intravenous infusion of 2 grams/8 hours daily for five days, followed by 4 grams/day orally for two weeks.

γ-(3,4,5-Trimethoxybenzamido)-butyric acid and its sodium salt are also effective to reduce blood cholesterol in humans, monkeys, rats, and other animals. When administered orally at a dose of 200 mg. per kg. body weight per day, γ-(3,4,5-Trimethoxybenzamido)-butyric acid has lowered blood cholesterol in rats.

In general, the (3,4,5-trialkoxybenzoyl)amino alkanoic and dialkanoic acids and salts described above will reduce blood cholesterol when used, as described, in amounts as set forth above. Such acids include (3,5-diethoxy-4-hydroxybenzoyl)-γ-amino butyric acid and its potassium salt, (3,4,5-trimethoxybenzamido)-ζ-octanoic acid, N-(3,4,5-triethoxybenzoyl)-L-aspartic acid, and N-(3,4,5-trimethoxybenzoyl)-α-amino adipic acid.

It is claimed:

1. A method for reducing serum blood cholesterol comprising administering to a warm-blooded animal in which lowering of the serum blood cholesterol is desired an effective amount of a compound having the formula:

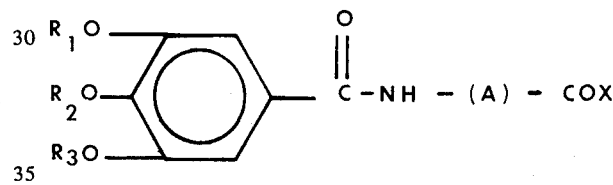

wherein $R_1$, $R_2$, and $R_3$ are hydrogen, methyl, ethyl, or propyl, and A is a saturated hydrocarbon radical substituted with one carboxylic acid group and containing 2 to 8 carbon atoms, and X is $-NH_2$.

* * * * *